United States Patent [19]

Chesterfield et al.

[11] Patent Number: 5,318,575
[45] Date of Patent: Jun. 7, 1994

[54] METHOD OF USING A SURGICAL REPAIR SUTURE PRODUCT

[75] Inventors: Michael P. Chesterfield, Norwalk; Ilya Koyfman, Orange, both of Conn.

[73] Assignee: United States Surgical Corporation, Norwalk, Conn.

[21] Appl. No.: 829,423

[22] Filed: Feb. 3, 1992

[51] Int. Cl.⁵ ............................................. A61B 17/00
[52] U.S. Cl. .................................. 606/151; 606/228; 606/231; 128/898; 623/13
[58] Field of Search ..................... 606/228, 231, 151; 623/13; 128/898

[56] References Cited

U.S. PATENT DOCUMENTS

| | | |
|---|---|---|
| 1,717,766 | 6/1929 | Eimler . |
| 1,950,799 | 3/1934 | Jones .. |
| 2,987,062 | 6/1961 | Ellison . |
| 3,105,493 | 10/1963 | Usher . |
| 3,111,945 | 11/1963 | Von Solbrig . |
| 3,113,115 | 12/1963 | Ziegler et al. . |
| 3,187,752 | 6/1965 | Glick . |
| 3,359,983 | 12/1967 | Northey . |
| 3,469,573 | 9/1969 | Florio . |
| 3,473,528 | 10/1969 | Mishkin et al. . |
| 3,565,077 | 2/1971 | Glick . |
| 3,570,497 | 3/1971 | Lemole . |
| 3,577,601 | 5/1971 | Mariani et al. . |
| 3,802,438 | 4/1974 | Wolvek . |
| 4,014,973 | 3/1977 | Thompson . |
| 4,037,603 | 7/1977 | Wendorff . |
| 4,043,344 | 8/1977 | Landi et al. . |
| 4,047,533 | 9/1977 | Perciaccante et al. . |
| 4,119,091 | 10/1978 | Partridge . |
| 4,137,394 | 1/1979 | Meihuizen et al. . |
| 4,201,215 | 5/1980 | Crossett et al. . |
| 4,263,904 | 4/1981 | Judet . |
| 4,279,248 | 7/1981 | Gabbay . |
| 4,356,138 | 10/1982 | Kavesh et al. . |
| 4,403,012 | 9/1983 | Harpell et al. . |
| 4,413,110 | 11/1983 | Kavesh et al. . |
| 4,455,273 | 6/1984 | Harpell et al. . |
| 4,512,346 | 4/1985 | Lemole . |
| 4,520,822 | 6/1985 | Menezes et al. . |
| 4,535,764 | 8/1985 | Ebert . |
| 4,557,264 | 12/1985 | Hinsch . |
| 4,583,541 | 4/1986 | Barry . |
| 4,620,542 | 11/1986 | Menezes et al. . |
| 4,625,717 | 12/1986 | Covitz . |
| 4,643,178 | 2/1987 | Nastari et al. . |
| 4,655,769 | 4/1987 | Zachariades . |
| 4,667,662 | 5/1987 | Titone et al. . |
| 4,730,615 | 3/1988 | Sutherland et al. . |
| 4,759,765 | 7/1988 | Van Kampen .................. 623/13 |
| 4,790,850 | 12/1988 | Dunn et al. ..................... 623/13 |
| 4,792,336 | 12/1988 | Hlavacek et al. . |
| 4,802,477 | 2/1989 | Gabbay . |
| 4,813,416 | 3/1989 | Pollak et al. . |
| 4,819,458 | 4/1989 | Kavesh et al. . |
| 4,886,691 | 12/1989 | Wincklhofer . |
| 4,896,668 | 1/1990 | Popoff et al. . |

(List continued on next page.)

FOREIGN PATENT DOCUMENTS 2730571 of 0000 Fed. Rep. of Germany .
3042699 of 0000 Fed. Rep. of Germany .
3244680 of 0000 Fed. Rep. of Germany .

OTHER PUBLICATIONS

Sirivella, et al., "Improved Technique for Closure of Medium Sternotomy Incision/Mersilene [Ethicon, Inc.] Tapes Versus Standard Wire Closure" J. Thorac. Cardiovasc. Surg., 1987; 94:591-5.

(List continued on next page.)

Primary Examiner—Stephen C. Pellegrino
Assistant Examiner—J. A. Schmidt

[57] ABSTRACT

Textile surgical articles are disclosed which are constructed in whole or in part from high tenacity low elongation fibers such as ultra-high molecular weight extended chain polyethylene high tenacity fibers. The products may be braided, woven or knitted, such as braided tapes, hollow braids and spiroid braids. The high tenacity low elongation fibers provide structures having greatly increased strength and decreased elongation, a combination of properties which is uniquely applicable and superior for repairing body tissue. The products may be plasma treated to reduce slip.

12 Claims, 2 Drawing Sheets

U.S. PATENT DOCUMENTS

| | | |
|---|---|---|
| 4,916,193 | 4/1990 | Tang et al. .......................... 606/231 |
| 4,920,959 | 5/1990 | Witzel et al. . |
| 4,942,875 | 7/1990 | Hlavacek et al. . |
| 4,943,292 | 7/1990 | Foux . |
| 4,944,753 | 7/1990 | Burgess et al. . |
| 4,944,974 | 7/1990 | Zachariades . |
| 4,955,913 | 9/1990 | Robinson . |
| 4,959,069 | 9/1990 | Brennan et al. . |
| 4,976,257 | 12/1990 | Akin et al. . |
| 4,987,665 | 1/1991 | Dumican et al. . |
| 5,002,574 | 3/1991 | May et al. ............................ 623/13 |
| 5,024,618 | 6/1991 | Tepic . |
| 5,059,213 | 10/1991 | Chesterfield et al. . |

OTHER PUBLICATIONS

Product brochure for Deknatel Inc. (Pfizer) Dekna—Band sternotomy closure system.

Miller et al., "Repair of Sternal Dehiscence Using a Harrington Compression System", Ann. Thorac. Surg., 45:684–685, Jun. 1988.

Product Brochure for Pilling (Fort Washington Pa. Sternal Approximation and Fixation System.

Mulch et al., "Closure of Longitudinal Sternotomy with Absorbable Sutures", Thorac. Cardiovasc. Surgeon, 34, 191–193 (1986).

Johnston, Jr. et al., Mersilene [Ethicon, Inc.] "Ribbon Closure of the Median Sternotomy: An Improvement Over Wire Closure" (1984) and Mersilene Product Literature.

Labitzke et al., "'Sleeve–Rope Closure' of the Median Sternotomy After Open Heart Operations", Thorac. Cardiovasc. Surgeon, 31, 127–128 (1983), pp. 127–128.

Kalush et al., "Peristernal Closure of Median Sternotomy Using Stainless Steel Bands" (1975), pp. 172–173.

Timmes et al., "A New Method of Sternal Approximation", Ann. Thorac. Surg., vol. 16, No. 5, May, 1973, pp. 544–546 [the Wolvek approximator].

Sanfelippo et al., "Nylon Bands for Closure of Median Sternotomy Incisions/An Unacceptable Method", Ann. Thorac. Surg., vol. 13, No. 4, Apr., 1972, pp. 404–406.

LeVeen et al., "Nylon–Band Chest Closure", Arch. Surg., vol. 96, Jan. 1968, pp. 36–39.

Goodman et al., "Technique of Closure of Median Sternotomy with Transternal Figure–of–Eight Wires", J. Cardiovasc., Surg., vol. 27, 1986, pp. 512–513.

Vincent, "Update on Sternal Osteosynthesis", Ann. Thorac. Surg., vol. 41, Feb. 1986, pp. 216–218.

Vincent, "Controlled Tension Osteosynthesis A Way To Prevent Or Cure The Cardiac Sternotomy Complicators".

Allied Signal Inc.'s Product brochure for SPECTRA extended chain polyethylene fibers.

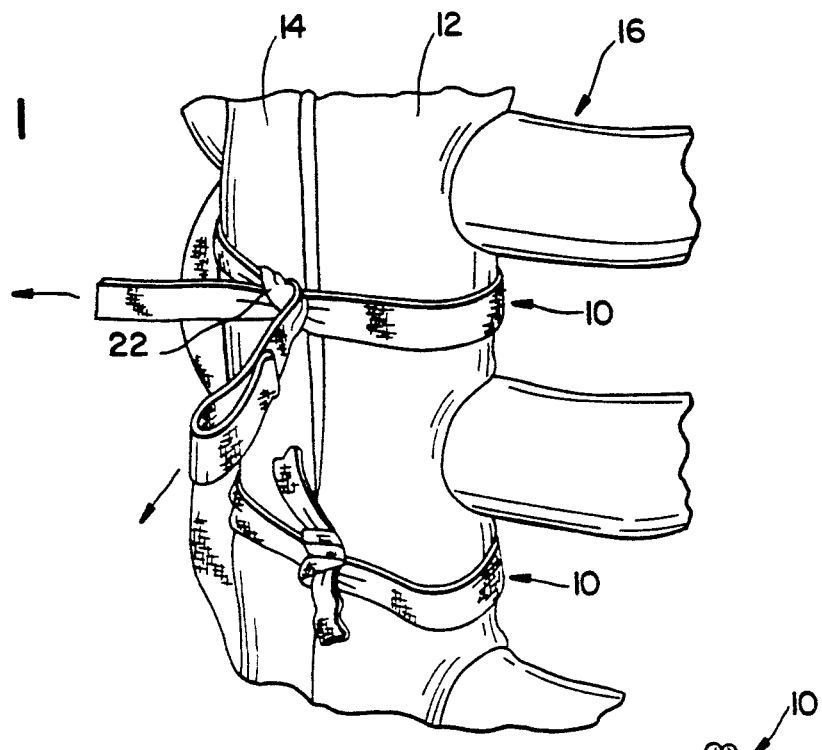
FIG. 1
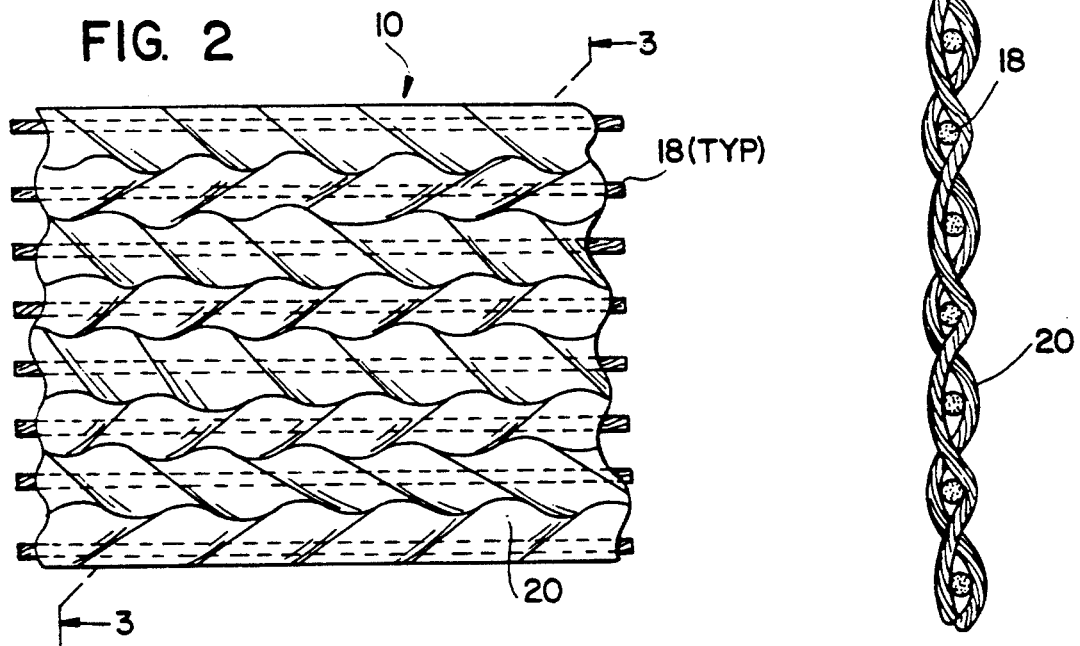
FIG. 2
FIG. 3

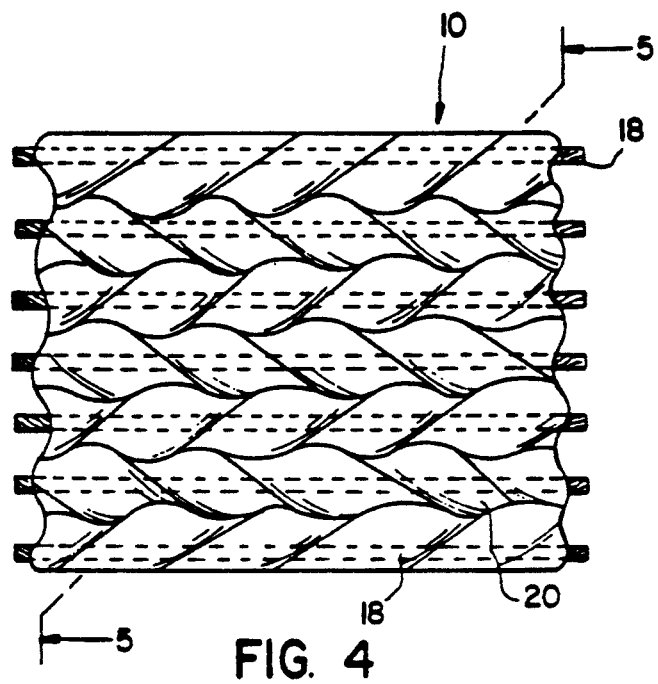
FIG. 4
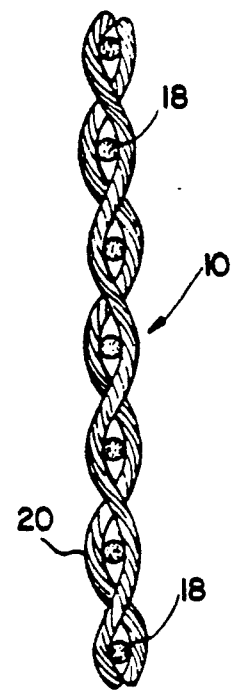
FIG. 5
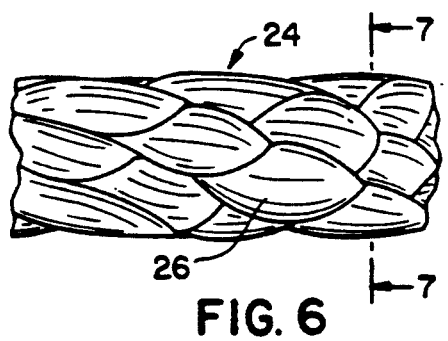
FIG. 6
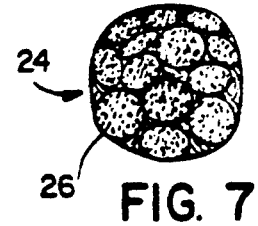
FIG. 7
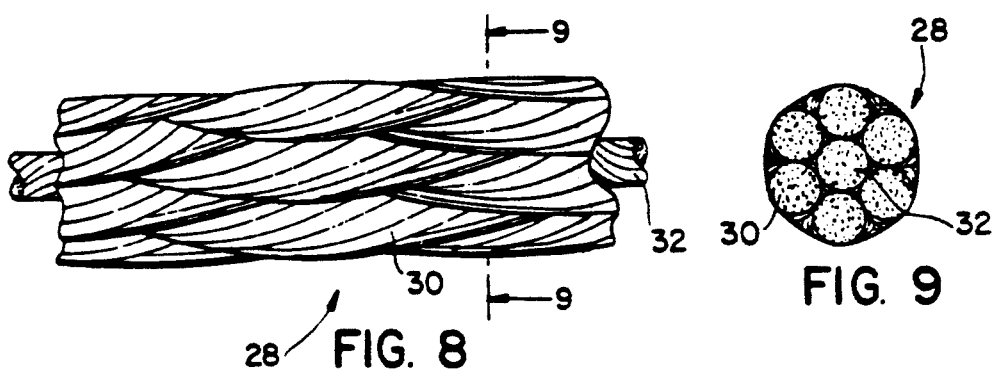
FIG. 8
FIG. 9

METHOD OF USING A SURGICAL REPAIR SUTURE PRODUCT

BACKGROUND OF THE INVENTION

1. Field of the Invention

The present invention relates to suture products for surgical repair of body tissue. In particular, the invention is directed to reinforced surgical repair products for repairing the human sternum after surgery.

2. Background of the Prior Art

Presently there are many known products for repairing human body tissue in areas where a repair may be required either as a result of an injury or during or after surgery. In particular, it is well known to utilize suture products in the form of elongated strands to repair human body tissue as well as utilizing two-part fasteners or metal staples for attaching body tissue after portions have been removed during surgery.

For example, sutures intended for repairing soft body tissue are usually constructed of a plurality of filaments and applied to the tissue with any number of surgical needles. More recently, a certain amount of emphasis as been placed upon repairing surgical bone utilizing an elongated surgical product either in the form of a flat band or in the form of a strand having the construction similar to a suture by simply utilizing a needle to penetrate the bone to apply the repair product to the bone in a manner which physically retains the separated bone portions together to promote permanent healing. One such example is disclosed in U.S. Pat. No. 4,535,764 to Ebert which relates to a surgical bone tie having a needle connected to one end of a band such that the band may be looped and arranged to be appropriately looped around the bone portions requiring repair.

U.S. Pat. No. 4,813,416 relates to a band assembly and method for sternum closing with which the sternum halves are brought to abutting closure utilizing a band having a needle at one end to facilitate looping the band in position to retain the sternum portions in adjacent butting contacting relation.

Numerous other products have been used to retain bone portions together to promote healing while numerous suture products have been used to retain soft tissue to retain healing.

While many attempts have been made to provide such products little emphasis has been applied to the physical strength characteristics of the components which form the actual suture or band product in order to provide the surgeon with precision control on the product. Moreover, control is required on the tissue to which the product is applied in a manner which will promote healing of the tissue, yet will not cause unnecessary cutting of the tissue when force is applied to the product and the force is in turn applied to the tissue.

A particularly desirable product for accomplishing these goals would preferably display substantial strength without significant elongation to facilitate retaining the tissue portions together. In the case of attaching separate bone portions of the sternum together after open heart surgery for example, it has been necessary to utilize metal wire filaments by looping the wire filaments around the sternum portions and actually twisting the filament ends together to form an attachment. The metal wire displayed sufficient strength to retain the bone portions together without elongation. However, the wire represented a relatively sharp nonabsorbable foreign body which remains embedded within the body tissue and thus presents a potential source of infection or other complications as a result of its presence within the body. Moreover, the relatively sharp characteristics of the wire present a danger of cutting into the bone during the application to the sternum. The sharp wire also presents a hazard to the surgeon and operating room personnel in that the wire may penetrate surgical gloves and cut the surgeon or attendant personnel, thereby creating a potential site for transmission of disease.

While utilization of wire sutures has been used and accepted during open heart surgery there remains room for improvement in the products used for strapping the split sternum portions together. Desirably, it would be best to provide a known metallic product which not only provides the strength to elongation characteristics of the metal sutures but which may be utilized to form a tying product for soft as well as hard tissue, in a manner which will minimize the dangers of cutting of the tissue in the surrounding areas. The present invention is directed to such a product.

SUMMARY OF THE INVENTION

In accordance with the present invention, textile surgical articles are disclosed which are made in whole or in part from high tenacity low elongation fibers such as ultra high molecular weight extended chain polyethylene high tenacity fibers. One such fiber is Spectra yarn from Allied Signal Corp. The products may be braided, woven or knitted, although braided tape, hollow braids and spiroid braids are preferred. The high tenacity low elongation fibers provide structures having greatly increased strength and decreased elongation.

In one embodiment, braided tapes are made from Spectra yarn. In an alternative embodiment braided tapes are made with Spectra runners and bioabsorbable, Dacron polyester and/or nylon fill yarns.

Further alternative embodiments include tubular braided structures having a core made in whole or in part from high tenacity low elongation fibers or spiroid braided structures made in whole or in part from high tenacity low elongation fibers.

In a preferred method of the invention, a braided tape reinforced with ultra-high molecular weight high tenacity fibers is used to join a divided sternum by tying, or other appropriate means. The tape has a very high strength, preferably equal to or greater than 35 kg. straight pull and more preferably greater than about 50 kg. straight pull, and low elongation at break, preferably below about 20%, more preferably below about 10 to 15%, and most preferably below about 5%.

BRIEF DESCRIPTION OF THE DRAWINGS

Preferred embodiments of the invention are described hereinbelow wherein:

FIG. 1 is a perspective view of a portion of a split human sternum illustrating one application of the present invention for retaining the split portions together to promote healing;

FIG. 2 is an enlarged view of the suture product shown in FIG. 1 illustrating one embodiment wherein the elongated product is a flat braided member and contains at least eight reinforcing filaments extending along the length;

FIG. 3 is a cross-sectional view taken along lines 3—3 of FIG. 2.;

FIG. 4 is an enlarged view of an alternative embodiment of the suture repair product of FIG. 2 wherein the elongated braided product contains at least seven reinforcing filaments extending along the length;

FIG. 5 is a cross-sectional view taken along lines 5—5 of FIG. 4;

FIG. 6 is a view of an alternative embodiment of the suture repair product wherein the elongated member is a spiroid braided member having a generally circular cross-section containing at least one elongated reinforcing member;

FIG. 7 is a cross-sectional view taken along lines 7—7 of FIG. 6;

FIG. 8 is a view of another alternative embodiment of the suture repair product wherein the elongated product is a hollow braided member having a generally circular cross-section and contains at least one elongated reinforcing member extending centrally thereof along the length; and FIG. 9 is a cross-sectional view taken along lines 9—9 of FIG. 8.

DETAILED DESCRIPTION OF THE PREFERRED EMBODIMENTS

Referring initially to FIG. 1 there is illustrated a sternum closure ribbon 10 constructed according to the present invention and positioned to retain portions 12,14 of a human sternum 16 together. The band 10 is preferably a braided product as shown in FIGS. 2 and 4 having a plurality of elongated filamentary reinforcing members of ultra high molecular weight polyethylene fibers. The fibers may be plasma treated to reduce slip characteristics of the yarn, if desired. In particular, such fibers as extended chain polyethylene high tenacity fibers (ECPE) marketed under the trademark SPECTRA ® by Allied-Signal Technologies, Petersburg, Va. 23804 are preferred as reinforcing members provided in the product of the present invention. SPECTRA 1000 yarn is suitable. These extended chain fibers exhibit a molecular weight generally between about 1 million to about 5 million but also may be as low as 500,000. They exhibit a very substantial degree of crystalline orientation (95–99%) and crystalline content (60–85%). As a result the fibers exhibit strengths from about 375 kpsi (thousands of pounds per square inch) to about 560 kpsi and tensile moduli of from about 15 msi (millions of pounds per square inch) to about 30 msi. The significant strength and stability of these fibers are caused by the high degree of molecular orientation. Moreover, since the fibers can be provided as multifilament or monofilament fibers which can be braided, woven, knitted or otherwise processed to form a textile product it will be readily appreciated that any number of reinforced textile products may be provided similar to the band 10 shown in the drawings, but with numerous alternative applications as will be described hereinbelow.

Referring now to FIG. 2, the band 10 shown in FIG. 1 is shown in greater detail as an elongated flat braided textile product having a plurality of high molecular weight fibers 18 extending along the length of the band.

The elongated fibers 18 are preferably made of ECPE marketed under the SPECTRA ® trademark and are surrounded by braided fibers 20 which may be of the bioabsorbable type. For example, fibers 20 may be made of any suitable bioabsorbable polymeric material such as polymers or copolymers of glycolide, lactide, p-dioxanone, polyester, polyamino acids and the like as disclosed in U.S. Pat. Nos. 2,668,162; 3,297,033; 3,636,956; 3,736,646; and 3,839,297. The number of reinforcing filaments 18 included in the braided band 10 shown in FIG. 2 is optional as is the specific construction of the band. For example, as seen in FIG. 4, there is an example of an alternative braided band construction having seven reinforcing filaments 18 of high molecular weight, high strength fibers of the type shown in FIG. 2. Furthermore, as seen in FIG. 7, there is an alternative elongated embodiment of spiroid braided construction of generally circular cross-section and comprised of one or more elongated filaments 26 of high molecular weight, high strength, with the remainder of the braid being of bioabsorbable filamentary materials to form a braided rope-like construction of generally circular cross-sectional configuration as shown in FIG. 7. Alternatively the braided product 22 may be constructed entirely of such high molecular weight, high strength, elongated filaments 24. Braid constructions having a circular cross-section are described in U.S. Pat. Nos. 3,565,077 and 5,019,093. Any number of combinations of bioabsorbable yarns, filamentary or otherwise, and/or non-absorbable, and high strength filaments are contemplated, depending upon the intended application.

In FIGS. 8 and 9 there is shown a hollow braid construction 28 having a sheath constructed of bio-absorbable yarns 30 and having a core 32 of high molecular weight, high strength filament. Any number of alternative combinations of 0 to 100% absorbable filamentary or otherwise, and/or non-absorbable yarns and high strength filaments are contemplated depending upon the intended application.

It will be appreciated that in addition to the examples which follow hereinbelow, numerous alternative textile constructions may be incorporated into the present invention to form a reinforced band for attaching body tissue such as a soft tissue or bone tissue without suffering from the disadvantages from presently known materials. For example, it is conceivable within the scope of the present invention to provide a woven structure containing a plurality of elongated high strength filaments 18 in the warp direction wherein the filler yarns are of a suitable bioabsorbable material such as polymers or copolymers of glycolide, lactide, p-dioxanone, polyester, polyamino acids and the like, or with fill yarns of a nonabsorbable material such as Dacron polyester or nylon. Likewise, knitted structures may be strengthened by reinforcement with high tenacity fibers. It will be appreciated that in each of the embodiments discussed herein the strength characteristics of the high tenacity, low elongation fibers 18 will provide the substantial force carrying capability to the elongate product while the fibers 20 surrounding the high strength filaments will provide the necessary structural support to the main fibers for forming the product. The surrounding fibers will also define the "hand" or "feel" of the band.

Accordingly, it is possible in one application to position the reinforced structure 10 about the split portions 13,14 of the human sternum 16 as shown in FIG. 1 whereby substantial force may be applied to the band by tying the band either by a knot 22 shown in FIG. 1, or by other techniques whereby significant force may be applied and retained to promote natural healing of the sternum portions 12,14, e.g. mechanical connecting devices such as buckles, etc. See, for example, U.S. Pat. No. 4,813,416. It has been found that such a band has a strength to elongation ratio comparable to stainless steel. The strength and load carrying capability of the elongated filaments 18 is sufficient to transmit substantial force to the sternum with minimum elongation occurring to the fibers thereby permitting the sternum portions to undergo a natural healing process. Furthermore, in addition to the textile processes of braiding and weaving it should be noted that alternative textile processes may be utilized including knitting techniques, provided that the final product contains a plurality of elongated high strength filaments 18,22 extending along at least the length of the product in the force-carrying direction to maintain the tissue portions together.

The braided product also may be made on a so-called spiroid braider by a method whereby a plurality of filament dispensers are moved in the same direction to different positions around a closed loop. In addition, the braid product may be produced by a conventional braiding process by directing a plurality of yarn dispensers along in equal and opposite undulating paths while directing the filaments or filler fibers toward a common braiding zone. In either process the final braided product will be manufactured to include a plurality of high strength, high molecular weight, high tenacity filaments as disclosed hereinabove, either as a component of the product, e.g. a core, or as the sole material used to construct the product. In addition, the yarn and/or product may be plasma treated depending upon the particular needs or intended application so as to reduce the perceived "slipperiness" of the product as desired.

For example, in any of the braided products disclosed herein the portions of the yarns may be of such high molecular weight, high tenacity filaments while the remaining portions are of absorbable or non-absorbable fibers or filaments. Further, the yarns may also be entirely of such high molecular weight, high tenacity filaments. For such products containing a core, the core may be as noted above, in combination with various types of fibers and/or filaments, absorbable or non-absorbable as described herein.

The final product could be provided with a surgical needle at one or both ends to facilitate insertion of the product into the body tissue whether the body tissue be soft skin tissue or hard bone tissue, or the needles may be utilized to facilitate looping the product into and out of spaces formed between the component members of the body such as the components forming the human sternum. Alternatively, the product could be provided with a needle at each end to facilitate ease of application to the body portions. In either event, the strength and the load carrying filaments 18 and the minimal elongation to strength percentage renders such filaments ideal for incorporation into a final product wherein body portions can be retained together to promote healing. In particular, the formation of a surgical suture repair product utilizing textile processes in combination with bioabsorbable filaments renders the incorporation of high tenacity, high strength, high molecular weight filaments 18 as an ideal combination to form a surgical suture repair product.

The following examples are provided for flat tapes and braids which can be utilized to tie two half portions of a human sternum to promote healing. In the examples which follow, all tapes or braids use Dacron polyester yarn. Braiding of the tapes or braids with Dacron yarns are noted for exemplary purposes only and such yarns may be appropriately substituted with any other suitable bioabsorbable or nonabsorbable yarns, as desired or appropriate for a particular construction. Of course, substitution of different yarns may require variations to the structure as required to accommodate changes in density and/or fiber denier. The fibers may be twisted or air entangled periodically to create a false twist.

EXAMPLE 1

A braided tape of Spectra 1000 high tenacity polyethylene multifilament fibers (60 filaments, 215 denier) was made on a 15 carrier flat tape braider with 7 parallel runners. This structure is shown in FIGS. 4 and 5. Tests showed the following properties.

| | |
|---|---|
| Denier = | 10,585 |
| Tape Thickness = | 0.66 mm |
| Tape Width = | 3.91 mm |
| Knot pull = | 47.5 kg |
| Straight pull = | 66.5 kg |
| Pick count = | 20 crossovers per inch |

The tape of this example was made with air entangled rather than twisted yarn. It is contemplated that the yarn could instead be twisted prior to braiding, with all or some of the yarn twisted in either the "s" or "z" directions. Twisted yarn should increase strength and decrease slipperiness of the tape.

EXAMPLE 2

A braided tape having multifilament Spectra 1000 runners (60 filaments, 215 denier) and Dacron fill yarns was made on a 17 carrier braider with 8 parallel runners. This structure is shown in FIGS. 2 and 3. The Dacron fill yarns were made with three plies of air entangled 100 denier, 54 filament Dacron type 55 yarn. The properties of the tape were measured as follows:

| | |
|---|---|
| Denier = | 7,551 |
| Tape Thickness = | 0.34 mm |
| Tape Width = | 3.14 mm |
| Knot pull = | 36.5 kg |
| Straight pull = | 53.6 kg |
| Elongation at break = | 3.4% |
| Pick count = | 26 crossovers per inch |

EXAMPLE 3

A braided tape is made with Spectra 1000 runners (60 filaments, 215 denier) and nylon fill yarn. The nylon fill yarn is made from three plies of 100 denier, 34 filament type 385 Dupont bright air entangled nylon yarns. The tape may be made to the desired width, thickness and pick count on any appropriate braider, such as a 15 carrier braider with 7 runners or a 17 carrier braider with 8 runners or a 21 carrier braider with 10 runners.

EXAMPLE 4

A braided tape is made with Spectra 1000 runners (60 filaments, 215 denier) and a bioabsorbable fill yarn such as a yarn made from a copolymer of glycolide and lactide. The bioabsorbable fill yarn may be twisted or air entangled and plied to a total denier of about 300 denier. the tape may be made to the desired width thickness and pick count on any appropriate braider, such as a 15 carrier braider with 7 runners or a 17 carrier braider with 8 runners or a 21 carrier braider with 10 runners.

EXAMPLE 5

A braided tape of plasma treated spectra 1000 high tenacity polyethylene multifilament fibers (60 filaments, 215 denier) was made on a 15 carrier flat tape braider with 7 parallel runners. Tests showed the following properties:

| | |
|---|---|
| Denier = | 5,338 |
| Tape Thickness = | 0.40 mm |
| Tape Width = | 3.21 mm |
| Knot pull = | 47.5 kg |
| Straight pull = | 66.5 kg |
| Elongation at break = | 8.6% |
| Pick count = | 25 crossovers per inch |

The tape of this example was made with air tangled rather than twisted yarn. It is contemplated that the yarn could instead by twisted prior to braiding, with all or some of the yarn twisted in each of the "s" or "z" directions.

The tape made from plasma treated yarn was perceptibly less slippery than the tape of Example 1, which may be desirable under some circumstances.

EXAMPLE 6

A suture of spiroid braid construction was made on a 15 carrier spiroid braider using Spectra 1000 yarn (60 filament, 215 denier). The braid is shown in FIGS. 6 and 7. The braid had the following properties.

| | |
|---|---|
| Denier = | 3,248 |
| Diameter = | 0.832 mm |
| Knot pull = | 32.4 kg |
| Straight pull = | 43.0 kg |
| Elongation at break = | 14% |

Spiroid sutures may be made with twisted yarn with a variety of carriers, such as 9, 12, 20 or 25 carriers, as desired to obtain a particular configuration.

EXAMPLE 7

A suture of hollow braid construction having a Spectra 1000 core was made, and is shown in FIGS. 8 and 9. Dacron air entangled bright polyester yarn (40 denier, 8 filament, type 55) was used on the carriers of an 8 carrier braider (4 carriers travelling in the S direction, 4 carriers travelling in the Z direction) to make a sheath surrounding a core of untwisted Spectra 1000 yarn. The properties of the suture were as follows.

| | |
|---|---|
| Denier = | 550 |
| Diameter = | 0.20 mm |
| Knot pull = | 3.9 kg |
| Straight pull = | 7.9 kg |
| Elongation at break = | 3.3% |

A wide variety of hollow braid constructions are contemplated. Thus, sutures having Spectra 1000 core or components can be made on braiders having 12, 16, 24, 28 or 32 carriers, and numerous yarns can be used to form a sheath surrounding the core, such as bioabsorbable yarn; Dupont Dacron polyester air entangled bright yarn (such as 100 denier, 54 filament type 55 bright yarn or 70 denier, 34 filament type 52 bright yarn); or Dupont air entangled nylon yarn (such as 40 denier, 13 filament type 335 bright yarn or 100 denier 34 filament type 385 bright yarn or 70 denier, 34 filament type 185 bright yarn or 55 denier 17 filament type 865 bright yarn, or 15 denier 7 filament type 180 bright yarn).

The core yarns may be twisted to condense the structure or plied to increase strength and denier. The sheath yarns may also be twisted, if desired.

In the foregoing examples, all physical tests were conducted at 73° F., 50% relative humidity on an Instron Corporation Model 4502 test apparatus. Knot pull tests were performed using a 6 inch gauge length with a 0.5 inch per minute crosshead speed. Straight pulls were made using a 10 inch gauge length with a 10 inch per minute crosshead speed. Yarn or tape grips were used, as appropriate.

While the foregoing description contains many specifics, it will be understood that numerous modifications may be made within the scope of the appended claims. By way of example, a wide variety of yarn substitutions may be made to arrive at various braided tape or hollow and spiroid suture configurations constructed in whole or in part from high tenacity reinforcing fibers. In addition, bioabsorbable and non-bioabsorbable yarns may be substituted as desired to achieve properties and characteristics suitable for a particular situation.

We claim:

1. A method for repairing split portions of body tissue comprising looping a flexible elongated member about the body tissue in a manner to attach the portions in adjacent engaged relation to promote natural healing thereof, said flexible member being formed at least in part of first fibers of ultra-high molecular-weight high tenacity material and at least second fibers which differ from said first fibers and are formed from a non-absorbable material, said first and second fibers being braided to form said elongated member.

2. The method of claim 1 wherein the molecular weight of said fibers is within the range of from about 500,000 to about 5 million.

3. The method of claim 2 wherein said fibers comprise high tenacity extended chain polyethylene fibers.

4. The method of claim 1 wherein said elongate member has an elongation to break below about 15%.

5. The method according to claim 1 wherein said elongate member is of a flat braided construction.

6. The method according to claim 1 wherein said elongate member is of hollow braid construction.

7. The method according to claim 6 wherein said hollow braid contains a core.

8. The method according to claim 1 wherein said elongated member is of spiroid braid construction.

9. The method according to claim 8 wherein said spiroid braid has a substantially circular cross-sectional shape.

10. The method according to claim 1 wherein said elongated member has a straight pull greater than about 35 kg.

11. The method according to claim 1 wherein said second non-absorbable fibers are formed from nylon.

12. The Method according to claim 1 wherein said second non-absorbable fibers are formed from polyester.

* * * * *